(12) United States Patent
Sogaro

(10) Patent No.: US 7,790,115 B2
(45) Date of Patent: Sep. 7, 2010

(54) PIPETTING APPARATUS

(75) Inventor: Alberto C. Sogaro, Kronberg (DE)

(73) Assignee: Dentaco Dentalindustrie-und Marketing GmbH, Bad Homburg (DE)

(*) Notice: Subject to any disclaimer, the term of this patent is extended or adjusted under 35 U.S.C. 154(b) by 907 days.

(21) Appl. No.: 11/485,858

(22) Filed: Jul. 13, 2006

(65) Prior Publication Data

US 2007/0014697 A1 Jan. 18, 2007

(30) Foreign Application Priority Data

Jul. 15, 2005 (EP) .............................. 05 015 476

(51) Int. Cl.
*B01L 3/02* (2006.01)
(52) U.S. Cl. .................. 422/100; 604/191; 604/197; 73/863.32; 73/864; 73/864.01; 73/864.11; 73/864.13
(58) Field of Classification Search ........ 604/82–93.01, 604/191, 197, 221; 422/100; 222/525; 73/863.32, 73/864, 864.01, 864.11, 864.13
See application file for complete search history.

(56) References Cited

U.S. PATENT DOCUMENTS

| | | | | | |
|---|---|---|---|---|---|
| 3,566,859 | A | * | 3/1971 | Schwartz | 600/578 |
| 3,659,749 | A | * | 5/1972 | Schwartz | 222/129 |
| 3,682,174 | A | * | 8/1972 | Cohen | 604/90 |
| 3,684,136 | A | | 8/1972 | Baumann | |
| 3,685,514 | A | * | 8/1972 | Cheney | 604/90 |
| 3,785,379 | A | * | 1/1974 | Cohen | 604/88 |
| 4,041,945 | A | * | 8/1977 | Guiney | 604/91 |
| 4,202,314 | A | * | 5/1980 | Smirnov et al. | 604/138 |
| 4,439,184 | A | | 3/1984 | Wheeler | |
| 4,464,174 | A | * | 8/1984 | Ennis | 604/90 |
| 4,644,807 | A | * | 2/1987 | Mar | 73/864.62 |
| 5,125,892 | A | * | 6/1992 | Drudik | 604/90 |
| 5,643,206 | A | * | 7/1997 | Fischer | 604/82 |
| 5,643,306 | A | * | 7/1997 | Schraga | 606/182 |
| 5,665,066 | A | * | 9/1997 | Fischer | 604/82 |

(Continued)

FOREIGN PATENT DOCUMENTS

| | | |
|---|---|---|
| WO | 9846136 | 10/1998 |
| WO | 9917820 | 4/1999 |

*Primary Examiner*—Brian R Gordon
(74) *Attorney, Agent, or Firm*—Quarles & Brady LLP

(57) ABSTRACT

A pipetting device including a pipetting unit (12) having an application chamber (26) and a first end (16) that is realized with a discharge opening (18), and a second, open end (20). In the vicinity of the second, open end (20) of the pipetting unit (12), a sleeve-like receptacle unit (14) is guided so that it can move axially on at least two sealing lips (22, 24) that project radially inward and are at some distance from each other, which is provided on the side facing the application chamber (26) of the pipetting unit (12) with a base element (28), and on the side facing away from the application chamber (26) has an opening (32) and which has, in the vicinity of its periphery, at least one opening (34), the axial dimensions of which are somewhat smaller than or equal to the distance between the sealing lips (22, 24). The receptacle unit (14) can be moved with respect to the pipetting unit (21) from a closed position into an activation position, in which an interior (36) of the receptacle unit (14) is in communication via the at least one opening (34) of the receptacle unit (14) with the application chamber (26) of the pipetting unit.

7 Claims, 1 Drawing Sheet

U.S. PATENT DOCUMENTS

| | | | |
|---|---|---|---|
| 5,695,465 A * | 12/1997 | Zhu | 604/82 |
| 5,830,193 A * | 11/1998 | Higashikawa | 604/191 |
| 5,865,804 A * | 2/1999 | Bachynsky | 604/134 |
| 5,971,953 A * | 10/1999 | Bachynsky | 604/90 |
| 6,149,626 A * | 11/2000 | Bachynsky et al. | 604/134 |
| 6,440,101 B1 * | 8/2002 | Grabenkort et al. | 604/89 |
| 6,902,543 B1 * | 6/2005 | Cherif-Cheikh et al. | 604/82 |
| 2001/0021820 A1 | 9/2001 | Lynn | |
| 2005/0075602 A1 * | 4/2005 | Cherif-Cheikh et al. | 604/87 |
| 2006/0116644 A1 * | 6/2006 | Norton | 604/187 |
| 2007/0129671 A1 * | 6/2007 | Mu | 604/82 |
| 2007/0167910 A1 * | 7/2007 | Tennican et al. | 604/110 |
| 2008/0214998 A1 * | 9/2008 | Kurek et al. | 604/93.01 |
| 2008/0234632 A1 * | 9/2008 | Hasegawa | 604/191 |

* cited by examiner

PIPETTING APPARATUS

CROSS REFERENCES TO RELATED APPLICATIONS

This application claims the priority benefit of European Patent Application No. 05 015 476.4 filed on Jul. 15, 2005.

STATEMENT REGARDING FEDERALLY SPONSORED RESEARCH

Not Applicable.

TECHNICAL FIELD

This invention relates to a pipetting apparatus comprising a pipetting unit in the form of a small tube that has a receptacle chamber and a first end that is realized with a discharge opening and a second, open end.

DESCRIPTION OF THE BACKGROUND ART

A pipetting device in the form of a small tube having a receptacle chamber and a first end with a discharge opening and a second open end is known in practice. One known pipetting unit is fabricated from plastic or glass. A suction device on the second, open end draws a liquid to be applied to a substrate into the receptacle through the discharge opening. The liquid to be applied can in turn be applied to a substrate or delivered into a reaction vessel. A sample of saliva or a similar substance can be added to the liquid to be applied can then be subjected to chemical or biochemical tests. The addition to the liquid of the substance to be analyzed takes place before the pipetting in a separate vessel.

SUMMARY OF THE INVENTION

The object of the invention is to provide a pipetting apparatus by means of which an application of a fluid substance to which with a substance to be analyzed has been added can be carried out in a simplified manner. The object is accomplished by providing a pipetting apparatus including a pipetting unit in the form of a small tube which has an application chamber, a first end that is realized with an discharge opening and a second, open end. In the vicinity of the second, open end of the pipetting unit, a sleeve-like receptacle unit is guided so that it can move axially on two sealing lips of the pipetting unit that project radially inward and are at some distance from each other, which receptacle unit is provided on the side facing the application space of the pipetting unit with a base element and which, on the side away from the application chamber, has an opening and which, in the vicinity of its peripheral surface has at least one opening, the axial dimensions of which are smaller than or equal to the distance between the sealing lips. The receptacle unit can be moved with reference to the pipetting unit out of a closed position into an activation position in which the interior of the receptacle unit is in communication by means of the at least one opening in the receptacle unit with the application space of the pipetting unit.

Preferably, the pipetting device includes a vessel that is formed by the receptacle unit, into which, by means of the opening, for example a substance to be analyzed can be introduced into a test liquid. The test liquid to which the test substance with the substance to be analyzed can be introduced into the application chamber of the pipetting unit by a displacement of the receptacle unit with reference to the pipetting unit without the need for additional equipment. Specifically, as a result of the displacement of the receptacle unit into the activation position, the fluid flows via the at least one opening in the receptacle unit into the application chamber of the pipetting unit and in this manner can be applied by means of the pipetting unit via its discharge opening onto a substrate or into a reaction vessel. In the closed position of the receptacle unit, the sealing lips prevent the test fluid from escaping via a ring-shaped gap between the receptacle unit and the pipetting unit to the environment and from flowing into the application chamber of the pipetting unit. When the receptacle unit is moved into the activation position, the at least one opening moves across the sealing lips that exert a sealing action in the direction of the application chamber, so that the fluid can then flow via the ring-shaped gap between the receptacle unit and the pipetting unit from the interior of the receptacle unit into the application chamber of the pipetting unit.

In one preferred exemplary embodiment of the pipetting device, the receptacle unit is provided with a cover element. The cover element closes the opening of the receptacle unit so that a fluid that is contained in the receptacle unit cannot flow out. When a sample held by a test swab such as a cotton swab is to be added to a test fluid that is located in the receptacle unit, the cover element, which can be realized in the form of a cap, for example, is removed, the swab is immersed in the test fluid and then extracted from it. The cover element is then placed back on the receptacle unit so that a homogenization with the test fluid to which the specimen has been added can then take place. Then the receptacle unit can be moved into the activation position, as a result of which the test fluid flows into the application chamber and can then be applied by means of the pipetting unit.

The cover element can be connected with the receptacle unit in a captive connection, for example by means of a film hinge, or it can also be realized in the form of a separate cap for the receptacle unit.

To prevent fluid from escaping from the pipetting unit via the discharge opening after an activation of the pipetting device, i.e. after the movement of the receptacle unit into the activation position, the pipetting unit can be provided with a closing element. This closing element can be molded in one piece onto the pipetting unit, or it can also form a separate component which is attached to the pipetting unit.

In another preferred embodiment of the pipetting device, the pipetting unit is formed by an elastically deformable, in particular soft plastic, so that the fluid contained in the application chamber of the pipetting unit ca be discharged via the discharge opening and out of the application chamber simply by applying manual pressure on the side of the pipetting unit.

To prevent the receptacle unit, which forms an inner sleeve, from accidentally slipping into the pipetting unit which is formed by an outer sleeve, the inner sleeve can have at least one ring-shaped groove which, by interacting with at least one of the sealing lips of the pipetting unit, defines the closed position and/or the activation position of the inner sleeve.

The pipetting apparatus incorporating the present invention can also be used for the mixing of a plurality of components of a multi-component system, whereby one component is initially placed in the receptacle unit and an additional component is placed in the pipetting unit. Thus, for example, after the specimen to be analyzed has been added to the component that is contained in the receptacle chamber, and after the receptacle unit has been pushed into the activation position, a mixing of the two components can take place in the receptacle chamber of the pipetting unit even before the application.

Another embodiment of the present invention is a pipetting apparatus having a plurality of receptacle units that are guided one inside another, which receptacle units are realized in the shape of pots and have on their side wall at least one opening which in the closed position is located between two sealing lips of the respective adjacent outboard receptacle unit, and which by moving the respective receptacle unit into the activation position creates a connection between the interiors of the respective adjacent receptacle units. In this manner, it becomes possible to mix a plurality of components of a multi-component system before the application of a fluid by means of the pipetting unit.

A filter device which is selective for large particles and/or for a defined substance can also be located in the vicinity of the tip of the pipette.

Additional advantages and advantageous configurations of the invention are described in greater detail below and in the claims with reference to the accompanying drawing.

BRIEF SUMMARY OF THE DRAWINGS

One exemplary embodiment of the pipetting device incorporating the present invention is illustrated schematically in the accompanying simplified drawings and is explained in greater detail below. In the drawings.

DETAILED DESCRIPTION OF THE PREFERRED EMBODIMENTS

Figure 1:
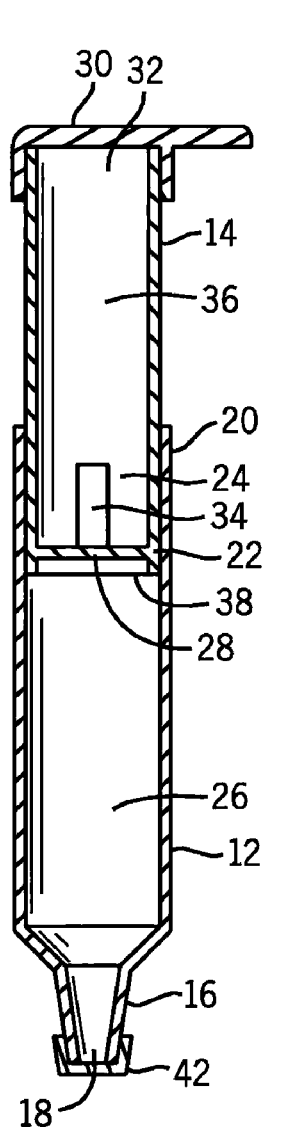
FIG. 1 is a longitudinal section through a pipetting device claimed by the invention in the deactivated position.
Figure 2:
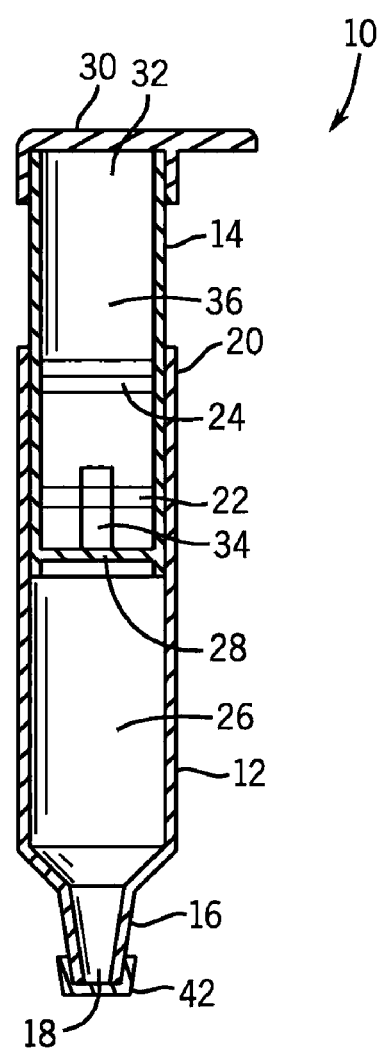
FIG. 2 shows the pipetting device illustrated in FIG. 1 in the activated position.

FIGS. 1 and 2 show a pipetting device 10 comprising a pipetting unit 12 and a receptacle unit 14 and can be used, for example, in the chemical or biochemical analysis of a test substance such as a saliva sample. The pipetting unit 12, which is an injection-molded plastic part, is made of a soft, elastically deformable plastic and comprises a first end 16, which is realized in the form of a pipetting tip having a discharge opening 18, and a second, open end 20. In the vicinity of the open end 20 of the pipetting unit 12, the receptacle unit 14 is guided so that it can move axially on two sealing lips 22 and 24 that project radially inward from an inner wall of the pipetting unit 12.

The receptacle unit 14, which has an interior 36, is realized essentially in the shape of a pot and is closed by means of a base element 28 on the side that faces an application chamber 26 of the pipetting unit 12. On the side facing away from the base element 28, the receptacle unit 14 has an opening 32 that can be closed by means of a cover element 30.

In the vicinity of its periphery, the receptacle unit 14, which is fabricated from a hard plastic and forms an inner sleeve, has openings 34, the axial dimensions of which are somewhat smaller than the distance between the sealing lips 22 and 24 that are realized in the form of a coil.

When the pipetting device 10 is used, the receptacle unit 14 that represents an inner sleeve is initially in the closed or blocking position illustrated in FIG. 1, in which the openings 34 between the two sealing lips 22 and 24 are located, so that there is no communication between the interior 36 of the receptacle unit 14 and the receptacle chamber 26 of the pipetting unit 12. A test fluid is in the interior 36 of the receptacle unit 14.

The sealing lip 22 is engaged in the closed position of the receptacle unit 14 in an annular groove 38 which is located approximately at the level of the base element 28 on the periphery of the receptacle unit 14 and thus defines the blocking position.

The cover element 30 which is realized in the shape of a cap is removed and a test rod or swab to which a saliva specimen has been added, for example, is dipped into the test fluid. A culture that consists of the saliva specimen is thereby added to the test fluid. The test rod is then extracted from the receptacle unit 14, and the cover element 30 is then placed on the receptacle unit 14 to close the opening 32.

Then, after a homogenization of the liquid contained in the interior 36 of the receptacle unit 14, the receptacle unit 14 can be pushed into the activation position illustrated in FIG. 2, in which the test liquid to which the saliva specimen has been added flows out of the interior 36 of the receptacle unit 14 via the openings 34 into the application chamber 26 of the pipetting unit 12. To prevent fluid from escaping from the pipetting unit 12 via the discharge opening 18 after an activation of the pipetting unit 12, i.e. after the movement of the receptacle unit 14 into the activation position, the pipetting 12 unit can be provided with a closing element 42. This closing element 42 can be molded in one piece onto the pipetting unit 12, or it can also form a separate component which is attached to the pipetting unit 12.

Then, for the application of the test fluid to which the saliva specimen has been added, a radial pressure is exerted manually on the pipetting unit, as a result of which the liquid can be applied via the discharge opening 18 to a nutrient substrate or injected into a reaction vessel.

While there has been shown and described what are at present considered the preferred embodiments of the invention, it will be obvious to those skilled in the art that various changes and modifications can be made therein without departing from the scope of the invention defined by the appended claims.

I claim:

1. A pipetting device comprising:
    a pipetting unit including an inner wall, a first end with a discharge opening, and a second, open end;
    a sleeve-like receptacle unit received in the second, open end of the pipetting unit, and including an open end and a closed end joined by a side wall;
    an application chamber defined by said inner wall between said closed end of said sleeve-like receptacle unit and said first end of said pipetting unit;
    at least two axially spaced sealing lips projecting inwardly from said inner wall that engage said sleeve-like receptacle unit, said sleeve-like receptacle unit being guided axially on said at least two sealing lips, said sleeve-like receptacle unit having at least one side opening formed in said side wall having an axial dimension, the axial dimension of said at least one side opening being less than or equal to the distance between the sealing lips, whereby the receptacle unit can be moved with respect to the pipetting unit from a closed position into an activation position, in which an interior of the receptacle unit is in communication via the at least one side opening of the receptacle unit with the application chamber of the pipetting unit.

2. The pipetting apparatus as claimed in claim 1, wherein the receptacle unit is provided with at least one cover element.

3. The pipetting apparatus as claimed in claim 2, wherein the cover element is connected with the receptacle unit in a captive manner.

4. The pipetting apparatus as claimed in claim 1, including a closing element which closes the discharge opening of the pipetting unit.

5. The pipetting apparatus as claimed in claim 1, wherein the pipetting unit is formed from an elastically deformable plastic.

6. The pipetting apparatus as claimed in claim 1, wherein the receptacle unit has at least one annular groove which by interaction with at least one of the sealing lips of the pipetting unit defines the closed position and/or the activation position of the receptacle unit.

7. The pipetting apparatus as claimed in claim 1, wherein the pipetting unit contains a mixing component which, during the movement of the receptacle unit into the activation position, is mixed with a mixing component that is contained in the receptacle unit.

* * * * *